US00PP10188P

United States Patent [19]

Carruth

[11] Patent Number: Plant 10,188

[45] Date of Patent: Jan. 13, 1998

[54] HYBRID TEA ROSE PLANT VARIETY NAMED 'WEKBLUSI'

[75] Inventor: Thomas F. Carruth, Altadena, Calif.

[73] Assignee: Weeks Wholesale Fose Grower, Inc., Upland, Calif.

[21] Appl. No.: 717,081

[22] Filed: Oct. 7, 1996

[51] Int. Cl.[6] ..... A01H 5/00

[52] U.S. Cl. ..... Plt./18

[58] Field of Search ..... Plt./18, 11, 14

[56] References Cited

U.S. PATENT DOCUMENTS

P.P. 9,289 9/1995 Wathen ..... Plt./18

*Primary Examiner*—Howard J. Locker

*Attorney, Agent, or Firm*—Christie, Parker & Hale, LLP

[57] ABSTRACT

A new variety of Hybrid Tea rose plant suitable for garden decoration, having flowers of silvery lavender coloration.

1 Drawing Sheet

BACKGROUND OF THE INVENTION

This invention relates to a new and distinct variety of Hybrid Tea Rose. The varietal denomination of the new variety is 'Wekblusi'. The plant is an upright growing seedling, suitable for outdoor garden decoration. It has as its seed parent the variety known as 'Delnible' (U.S. Plant Pat. No. 4,671) and as its pollen parent the variety known as 'Arogrewod', U.S. Plant Pat. No. 6,861.

SUMMARY OF THE INVENTION

Among the features which distinguish the new variety from other presently available and known commercial rose cultivars of which I am aware are the following combination of characteristics: its moderately small hooked prickles, its strong penetrating fragrance of damask rose and citrus blossom, and its flower coloration of silvery lavender. 'Wekblusi' may be asexually propagated by cuttings, budding, or grafting.

Asexual reproduction of the new variety by budding as performed in Kern County and Upland Calif., shows that the foregoing and other distinguishing characteristics come true to form and are established and transmitted through succeeding propagations.

COMPARISON WITH PARENTS

The new rose may be distinguished from its seed parent, 'Delnible' by the following combination of characteristics: whereas 'Wekblusi' produces flowers of a silvery lavender coloration, 'Delnible' produces flowers of a significantly darker lavender color. The new seedling bears flowers with about 22 to 28 petals, whereas the seed parent bears flowers with 28 to 35 petals. Whereas 'Wekblusi' produces a very high percentage of long stems bearing one flower, 'Delnible' tends to produce more stems with clusters of flowers.

The new variety may be distinguished from its pollen parent, 'Arogrewod' by the following combination of characteristics: whereas 'Wekblusi' bears flowers of a silvery lavender coloration, 'Arogrewod' bears flowers with a distinctly lighter under petal coloration and a stronger blush color on the upper petal side. The pollen parent has a rounded medium-height plant habit at maturity, whereas the new seedling has a taller, more upright mature plant growth habit.

BRIEF DESCRIPTION OF ILLUSTRATION

The accompanying photograph illustrates specimens of the new variety and shows the flowering thereof from bud to full bloom depicted in color as nearly correct as it is possible to make in a color illustration of this character. Throughout this specification, color values are based upon the Colour Chart of The Royal Horticultural Society of London, England, except where common terms of color definition are employed.

DESCRIPTION OF THE NEW VARIETY

The following description is of rose plants of the new cultivar grown outdoors in Upland, Calif. in the month of August. Phenotypic expression may vary with environmental, cultural and climatic conditions, as well as differences in conditions of light and soil.

FLOWER

The new variety bears its flowers usually singly, sometimes in clusters of two to three or more per stem. Flowers are borne in irregular flat to rounded clusters on strong long stems (about 48 to about 60 cms.). Outdoors the plant blooms abundantly and nearly continuously during the growing season. The flowers have a strong penetrating citrus-like to damask fragrance.

BUD

The peduncle is about 5.5 to about 8 cms., of average to heavy caliper, and usually erect. It is moderately rough, with many stipitate glands and some small prickles. Peduncle color is between 144A and 138A.

Before the calyx breaks, the bud is about 1.8 to about 2.5 cms. in diameter at the widest point, about 2.5 to about 3.3 cms. in length, and pointed to ovoid in shape. The surface of the bud bears numerous stipitate glands, usually with slender entire foliaceous parts extending beyond the tip of the bud equal to about ½ or more of its length. Bud color is between 144A and 138A.

The inner surface of the sepals is covered with very fine wooly tomentum; sepal margins are lined with many stipitate glands and some hairs.

As the petals open, the bud is about 2.4 to about 3 cms. in diameter at the widest point, and about 3.5 to about 4.5 cms. in length, and very pointed to ovoid to urn-shaped in form. The color of the under surface of the newly opened petals is between 65D and 56D sometimes lightly blushed with between 65B and 55B. At the point where the petal attaches, there is a small zone washed with near 154D in coloration. The color of the upper surfaces of the newly opened petals is between 65D and 56D. At the point on the upper surface where the petal attaches, there is a small defined zone of near 2B in coloration. The bud opens up well and is generally not prevented from opening by wet, cold, hot or dry weather.

BLOOM

When fully open, the bloom ranges from about 9.5 to about 13 cms. in diameter. Petalage is double with about 22 to 28 petals and about 1 to 7 petaloids arranged regularly. When partially open, the bloom form is very high centered, and the petals are moderately spiraled with petal edges somewhat rolled outward. When fully open, the bloom form is more cupped, and the petals are somewhat cupped with petal edges somewhat rolled outward.

PETALS

The substance of the petals is somewhat heavy and of medium thickness, with upper surfaces somewhat satiny to slightly velvety and under surfaces moderately shiny to satiny. The outer petals are nearly round to broadly obovate in shape with apices somewhat rounded. The inner petals are more broadly obovate in shape with apices somewhat rounded.

NEWLY OPENED FLOWER

The under surface of the outer, intermediate and inner petals is between 56D and 65D. At the point where the petal attaches, there is a small zone washed with near 154D in coloration.

The upper surface of the outer petals is between 56D and 65D. Sometimes at the outermost edge of the petals, the coloration is lightly blushed with between 65B and 55B. At the point where the petal attaches, there is a small defined zone of between 2B and 5C in coloration.

The upper surface of the intermediate and inner petals is of similar coloration to the upper surface of the outer petals but without any blush coloration.

The general tonality of the newly opened flower is between 65D and 56D, sometimes lightly blushed at the outer petal edges with between 65B and 55B.

THREE DAY OLD FLOWER

The under and upper surface of the outer and inner petals is lighter than between 65D and 69D. At the point where the petal attaches on the under surface, there is a very small zone of near 155D. At the point where the petal attaches on the upper surface, there is a small zone of near 4C.

The general tonality of the three day old flower is lighter than between 65D and 69D.

On the spent bloom, the petals usually drop off cleanly.

In August, blooms on the bush growing outdoors generally last from four to five or more days. Cut roses grown outdoors and kept at normal indoor living temperatures generally last from five or more days.

MALE REPRODUCTIVE ORGANS

There are many stamens (approximately 85) arranged regularly about the pistil; a few are mixed with petaloids or tucked in the calyx. The filaments are uneven in length varying from medium to long, most with anthers. The anthers are medium to large for the class and all open approximately at the same time. Anther color is near 17C when immature and near 166B at maturity. Pollen is very abundant and near 15D in color.

FEMALE REPRODUCTIVE ORGANS

Pistils vary in number (approximately 70). The styles are moderately uneven, average to long in length, somewhat thin in caliper, and somewhat loosely bunched. Stigma and style color is near 11C. Ovaries are usually all enclosed in the calyx.

Hips are of average length, nearly round to ovoid in shape, and near 24A in color when fully ripe. The hip surface is moderately smooth with somewhat thick fleshy walls. Seeds are average in number (approximately 15 to 22), and medium to large in size.

FOLIAGE

The compound leaves are usually comprised of three to seven leaflets and are borne abundantly. The leaves are about 8 to about 13 cms. in length and about 7.5 to about 11.5 cms. in width at the widest point, moderately heavy to leathery in texture, and somewhat semi-glossy to matte in finish. The leaflets are about 4.5 to about 7.5 cms. in length and about 3 to about 4.5 cms. in width at the widest point, somewhat oval to ovate in shape with moderately acute apices and round bases. Their margins are usually simply serrate.

The upper surface of the mature leaf is between 139A and 147A. The under surface of the mature leaf is between 148B and 191B. The upper surface of the young leaf is near 146B, often heavily suffused with between 183C and 187A. The under surface of the young leaf is near 144A, heavily suffused with between 183A and 183B.

The rachis is average in caliper and somewhat rough. The upper side is shallowly grooved with some stipitate glands on the edges of the grooves. The under side of the rachis is moderately smooth with few stipitate glands and very small prickles.

The stipules are medium in length with medium width and straight points that usually turn out at an angle of less than 45 degrees.

The plant displays an average degree of resistance to powdery mildew and blackspot as compared to other commercial varieties grown under comparable conditions in Upland, Calif.

GROWTH

The plant has a very upright tall habit (about 170 to about 200 cms. in height and about 100 to about 140 cms. spread at the widest point), with full branching. It exhibits very vigorous growth and the canes are of medium to heavy caliper for the class.

The color of the major stems is near 148B. They bear very few moderately small prickles which are about 0.3 to about 0.5 cms. The prickles are hooked severely downward and short with a moderately narrow base; prickle color is near 166A.

The color of the branches is between 136B and 144A. They bear a few moderately small prickles which are of similar size and shape to the large prickles on the major stems; prickle color is between 164A and 164B.

The color of the new shoots is near 144A often moderately suffused on the side facing the sun with between 183B and 183C. They bear a few moderately small prickles which are of similar size and shape to the large prickles on the major stems; prickle color is near 181A.

I claim:

1. A new and distinct variety of Hybrid Tea rose plant substantially as described and illustrated herein.

* * * * *

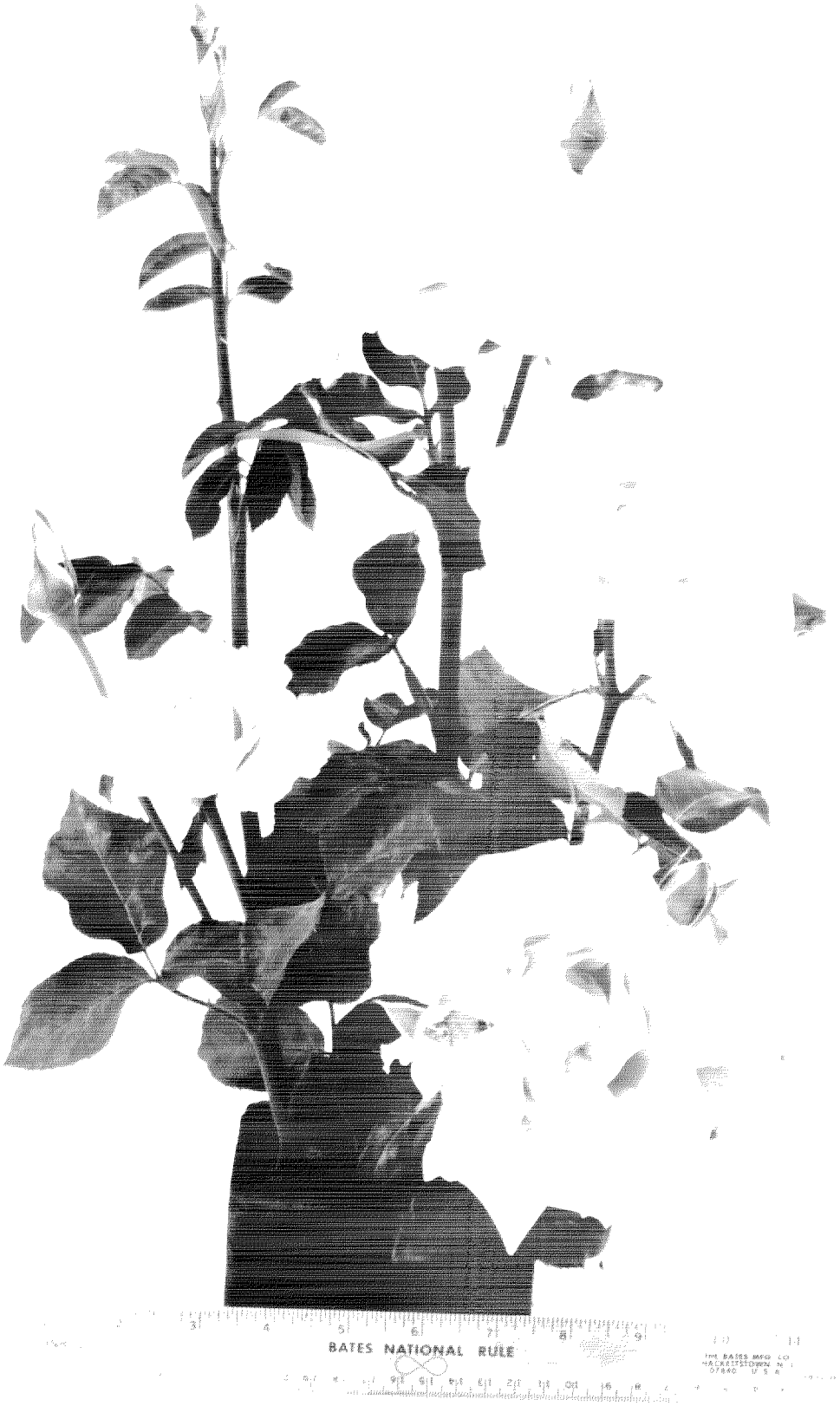
BATES NATIONAL RULE

UNITED STATES PATENT AND TRADEMARK OFFICE

CERTIFICATE OF CORRECTION

PATENT NO. : Plant 10,188
DATED : January 13, 1998
INVENTOR(S) : Thomas F. Carruth It is certified that error appears in the above-indentified patent and that said Letters Patent is hereby corrected as shown below:

Item 73, the Assignee should read
-- Weeks Wholesale Rose Grower, Inc. --

Signed and Sealed this

First Day of December, 1998

*Attest:*

Bruce Lehman

BRUCE LEHMAN

*Attesting Officer*

*Commissioner of Patents and Trademarks*